(12) United States Patent
Greenleaf et al.

(10) Patent No.: US 8,734,350 B2
(45) Date of Patent: May 27, 2014

(54) SYSTEM AND METHOD FOR CORRECTING ERRORS IN SHEAR WAVE MEASUREMENTS ARISING FROM ULTRASOUND BEAM GEOMETRY

(75) Inventors: James F Greenleaf, Rochester, MN (US); Shigao Chen, Rochester, MN (US); Heng Zhao, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 56 days.

(21) Appl. No.: 13/410,780

(22) Filed: Mar. 2, 2012

(65) Prior Publication Data

US 2012/0226158 A1     Sep. 6, 2012

Related U.S. Application Data

(60) Provisional application No. 61/449,354, filed on Mar. 4, 2011.

(51) Int. Cl.
*A61B 8/00*     (2006.01)
(52) U.S. Cl.
USPC ............................ 600/437; 600/438; 600/443

(58) Field of Classification Search
USPC ................................. 600/407, 437, 438, 443
See application file for complete search history.

(56) References Cited

U.S. PATENT DOCUMENTS

| | | | |
|---|---|---|---|
| 8,118,744 B2* | 2/2012 | Palmeri et al. | 600/437 |
| 2010/0010346 A1* | 1/2010 | Greenleaf et al. | 600/438 |
| 2011/0301465 A1* | 12/2011 | Waki | 600/445 |

* cited by examiner

*Primary Examiner* — Peter Luong
(74) *Attorney, Agent, or Firm* — Quarles & Brady, LLP

(57) ABSTRACT

A system and method for measuring mechanical properties of a tissue using an ultrasound system is provided. Ultrasound energy is applied to the tissue using the ultrasound system in order to produce shear waves that propagate in the tissue. Measurement data are then acquired by directing ultrasound detection pulses into the tissue. Information about the intensity field of the ultrasound energy used to produce the shear waves is obtained and used to produce a correction factor. This correction factor is applied to the measurement data to correct the measurement data for errors arising from the geometry of the ultrasound energy used to produce the shear waves. From the corrected measurement data, mechanical properties of the tissue are calculated.

13 Claims, 5 Drawing Sheets

SYSTEM AND METHOD FOR CORRECTING ERRORS IN SHEAR WAVE MEASUREMENTS ARISING FROM ULTRASOUND BEAM GEOMETRY

CROSS-REFERENCE

This application is based on, claims the benefit of, and incorporates herein by reference U.S. Provisional Application Ser. No. 61/449,354, filed Mar. 4, 2011, and entitled, "METHOD FOR CORRECTING ERRORS IN SHEAR WAVE MEASUREMENTS ARISING FROM ULTRASOUND BEAM GEOMETRY."

STATEMENT REGARDING FEDERALLY SPONSORED RESEARCH

This invention was made with government support under EB002640 and DK082408 awarded by the National Institutes of Health. The government has certain rights in the invention.

BACKGROUND OF THE INVENTION

The present invention relates generally to systems and methods for ultrasound and relates, more particularly, to systems and methods for ultrasound vibrometry, in which ultrasound is used to measure mechanical properties of a material or tissue of interest.

Characterization of tissue mechanical properties, particularly the elasticity or tactile hardness of tissue, has important medical applications because these properties are closely linked to tissue state with respect to pathology. For example, breast cancers are often first detected by the palpation of lesions with abnormal hardness. In another example, a measurement of liver stiffness has been used as a non-invasive alternative for liver fibrosis staging.

Recently, an ultrasound technique for measuring mechanical properties of tissues, such as stiffness and viscosity, called shear-wave dispersion ultrasound vibrometry ("SDUV") was developed. This SDUV technique is described, for example, in co-pending U.S. Pat. Nos. 7,785,259 and 7,753,847, which are herein incorporated by reference in their entirety. In these and similar methods, a focused ultrasound beam, operating within FDA safety limits, is applied to a subject to generate harmonic shear waves in a tissue of interest. The propagation speed of the induced shear wave is frequency dependent, or "dispersive," and relates to the mechanical properties of the tissue of interest. Shear wave speeds at a number of frequencies are measured by pulse echo ultrasound and subsequently fit with a theoretical dispersion model to inversely solve for tissue elasticity and viscosity. These shear wave speeds are estimated from the phase of tissue vibration that is detected between two or more points with known distance along the shear wave propagation path.

The shear wave speed measured with ultrasound vibrometry and related techniques is often biased such that it is greater than the true shear wave speed. This bias is position dependent and influenced by the three-dimensional structure of the ultrasound beam used to produce the shear waves. For example, the bias is larger closer to the sources of the ultrasound energy that produced the shear waves, and smaller when farther away from the sources.

In addition to the three-dimensional shape of the ultrasound push beam, the ultrasound detection beam used for shear wave detection also has a three-dimensional distribution. This means that pulse-echo detection cannot measure tissue motion at an infinitesimal point, but rather measures the averaged tissue motion within the small, but finite, detection beam dimension. This three-dimensional structure of the ultrasound detection beam can also have an impact on shear wave speed estimation. The overall result is that shear wave speed measurements are influenced by the beam shape of the ultrasound used for shear wave generation, as well as that used for detection. The ultrasound beam shape depends on where the ultrasound energy is electronically focused; therefore, shear wave speed measurements will be position dependent, even in a media with uniform stiffness, and, thus, a uniform shear wave speed.

Generally, shear wave speed measurements are depth dependent and biased towards overestimation. Shear wave speed measurements can also depend on the distance between the push beam and the detection beam. In general, measured shear wave speed is higher when detection is closer to the push beam and, thus, overestimated. This overestimation is exacerbated at shallow focal depths where the force field has split peaks.

It would therefore be desirable to provide a system and method for correcting measurements of shear wave speed for biases introduced by ultrasound push and detection beam shape and spacing.

SUMMARY OF THE INVENTION

The present invention overcomes the aforementioned drawbacks by providing a system and method for correcting shear wave measurements, including shear wave speed or shear wave attenuation, for errors arising from the geometry of an ultrasound beam used to produce said shear waves. Ultrasound energy is applied to a tissue using an ultrasound system in order to produce shear waves that propagate therein. Measurement data are then acquired by directing ultrasound detection pulses into the tissue. Information about the intensity field of the ultrasound energy used to produce the shear waves is obtained and used to produce a correction factor. Such information may be, for example, information about the geometry of the intensity field. For example, the information may be obtained from a mathematical model of the intensity field. This correction factor is applied to the measurement data to correct the measurement data for errors arising from the geometry of the ultrasound energy used to produce the shear waves. From the corrected measurement data, mechanical properties of the tissue may be calculated.

It is another aspect of the invention to provide a method for measuring mechanical properties of a tissue using an ultrasound system in which ultrasound energy is applied to the tissue by the ultrasound system in order to produce shear waves that propagate therein, and in which measurement data is acquired from the shear waves by directing ultrasound detection pulses into the tissue with the ultrasound system. A correction factor is obtained by interrogating a look-up table that contains shear wave speed measurements acquired from multiple locations within each of a plurality of different tissue phantoms having known mechanical properties and, using this correction factor, the acquired measurement data is corrected for errors that arise from the geometry of the applied ultrasound energy. From this corrected measurement data, mechanical properties of the tissue are calculated.

It is yet another aspect of the invention to provide a method for measuring mechanical properties of a tissue using an ultrasound system, in which ultrasound energy is applied to the tissue by the ultrasound system in order to produce shear waves that propagate therein, and in which measurement data is acquired from the shear waves by directing ultrasound detection pulses into the tissue with the ultrasound system.

Using the acquired measurement data, mechanical properties such as stiffness or viscosity of the issue are calculated using a model that related the acquired measurement data and a single shear wave frequency to the desired mechanical properties.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
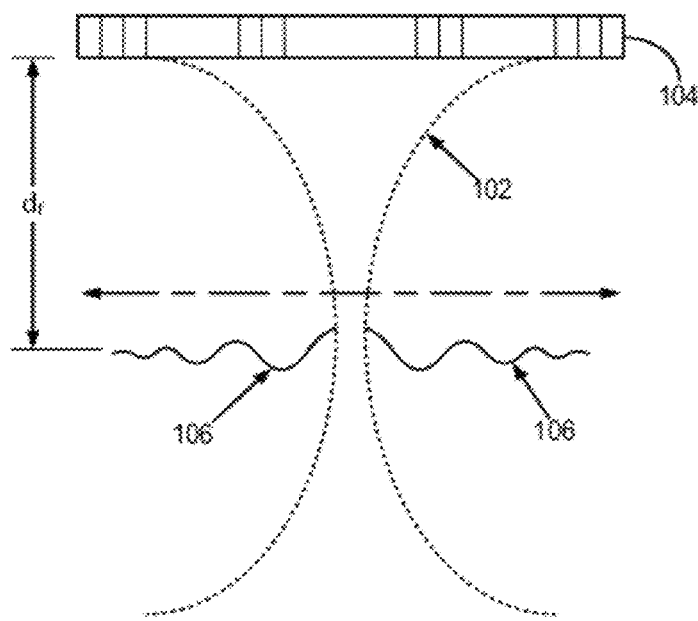
FIG. 1 is a pictorial representation of shear waves being produced in a medium by way of focused ultrasound energy.

Mechanical properties of tissue, such as elasticity and viscosity, are related to tissue health states and have important clinical applications for the diagnosis of diseases. For example, non-invasive measurements of liver stiffness may reduce the need for invasive liver biopsies used for liver fibrosis staging. The propagation characteristics of a shear wave, such as propagation speed and attenuation, are governed by the stiffness and viscosity of the tissue within which they propagate. Therefore, shear waves may be used for measurements of tissue stiffness and viscosity. Referring to FIG. 1, to generate shear waves in a tissue using ultrasound, a long-duration, focused ultrasound beam 102 generated by a transducer 104 is usually used to displace the tissue at a beam focus, a distance approximately $d_f$ from the transducer 104 and, thereby, generate shear waves 106 that propagate laterally outwards from the beam focus.

Figure 2:
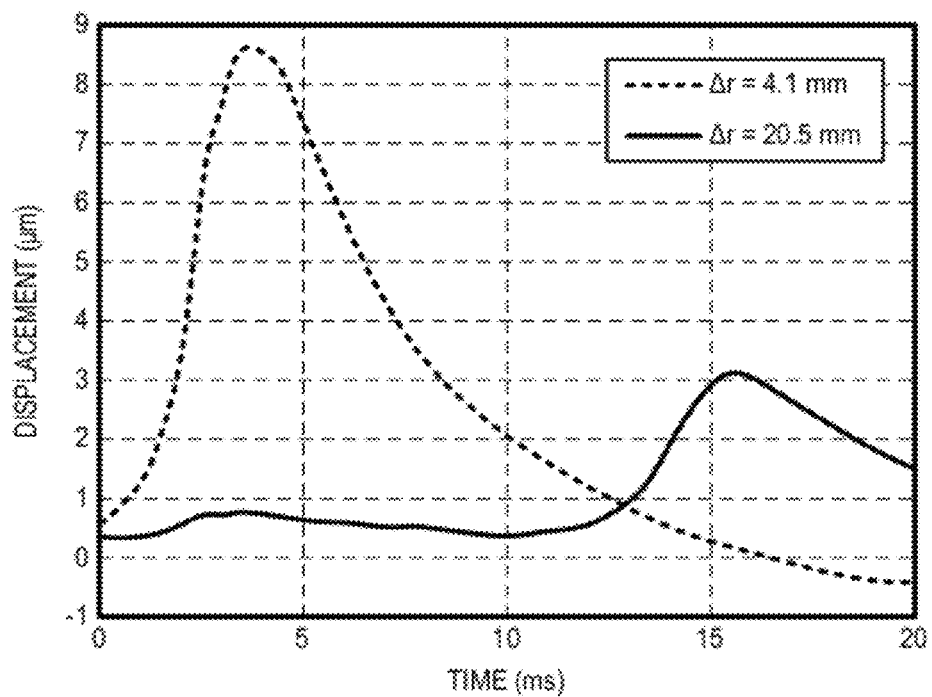
FIG. 2 is a graph illustrating measurements of a shear wave at two different lateral distances away from an ultrasound focal region.

Pulse echo ultrasound can be used to detect tissue motions due to the propagation of shear waves. Referring to FIG. 2, exemplary measurements of a shear wave detected at two different locations are illustrated. The first measurement location is 4.1 mm laterally away from the focal region of the push beam and the other is 20.5 mm from the focal region. Shear wave speed can be calculated by:

$$c_s = \frac{\Delta r}{\Delta t}; \tag{1}$$

where $\Delta r$ is the propagation distance over the time duration $\Delta t$. For example, shear wave speed can be calculated from the solid curve in FIG. 2 to be $c_s$=20.5/15.8=1.30 m/s, where 20.5 mm is the distance the shear wave travels from the push origin within 15.8 ms, which is the arrival time of the shear wave as indicated by the peak displacement of the solid curve. Similarly, the shear wave speed can be calculated from the arrival time of the dashed curve in FIG. 2, or even the difference between the dashed and solid curves:

$$c_s = \frac{(20.5 - 4.1)}{(15.8 - 3.7)} = 1.36 \ m/s; \tag{2}$$

where 3.7 ms is the arrival time of the shear wave detected at the location 4.1 mm from the push origin. The shear modulus, $\mu$, of the medium is related to shear wave speed, $c_s$, and medium density, $\rho$, through the following relationship:

$$c_s = \sqrt{\frac{\mu}{\rho}}. \tag{3}$$

For most applications, the tissue density, $\rho$, can be assumed to be 1000 kg/m$^3$. Therefore, tissue stiffness, $\mu$, can be calculated from Eqn. (3) if the shear wave speed, $c_s$, is measured by the aforementioned method.

Figure 3:
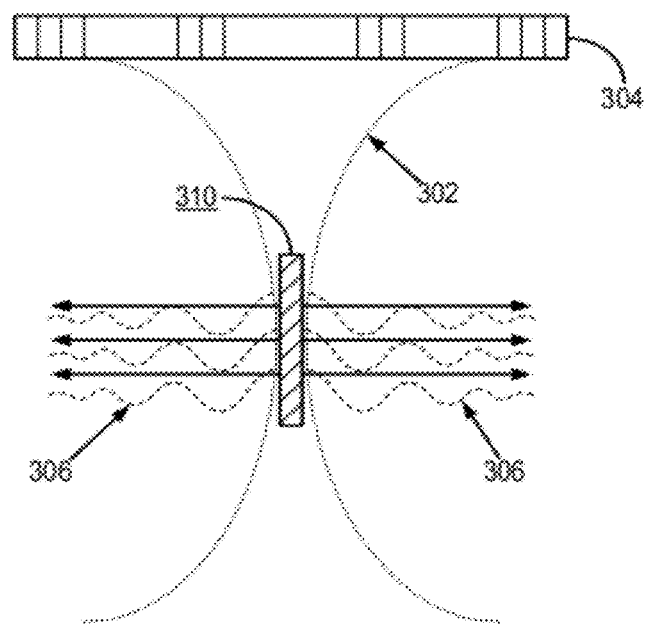
FIG. 3 is a pictorial representation illustrating the focal region of a focused ultrasound beam as producing a line force.
Figure 4:
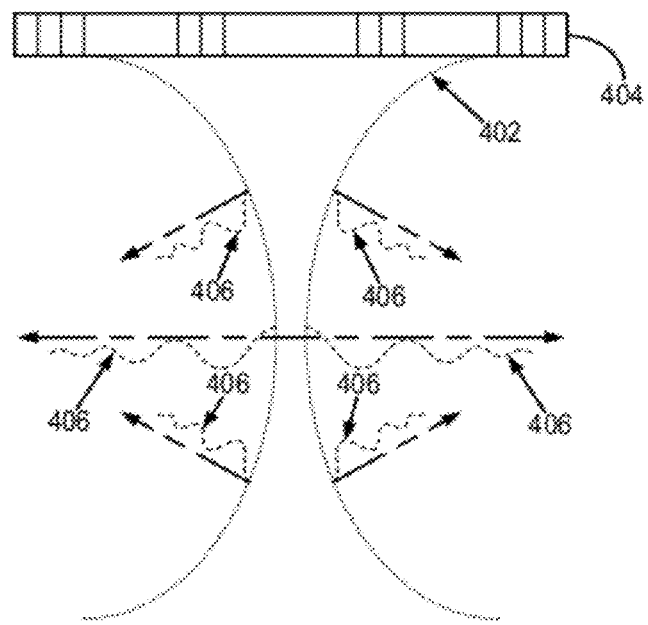
FIG. 4 is a pictorial representation illustrating the production of shear waves propagation in multiple directions in response to a focused ultrasound beam.

Referring to FIG. 3, in the analysis above, it is assumed that the ultrasound push beam 302 generated by the transducer 304 can be approximated as a line force 310 in the focal region and that the produced shear waves 306, therefore, propagate only in the horizontal direction, as shown in FIG. 3. As illustrated, this is the case when the push beam is vertical, but it is noted that, if the push beam is steered, the shear wave may propagate perpendicular to the push beam, and therefore would not be horizontal. Thus, in reality, the force field from a focused ultrasound push beam 302 is not a line force, but has a three-dimensional distribution. Referring to FIG. 4, the ultrasound push beam 402 is again represented as being generated by the transducer 404, but FIG. 4 more accurately shows that the shear waves 406 are generated from areas both proximal and distal to the focal region. In addition, the ultrasound push beam 402 has a thickness in the elevational direction of the transducer 404, which is the out-of-plane direction in FIG. 4. This thickness can also generate shear waves that will be detected at lateral positions. When the assumptions of FIG. 3 are violated, bias can be introduced to shear wave speed measurements and, therefore, tissue stiffness estimations.

Figure 5:
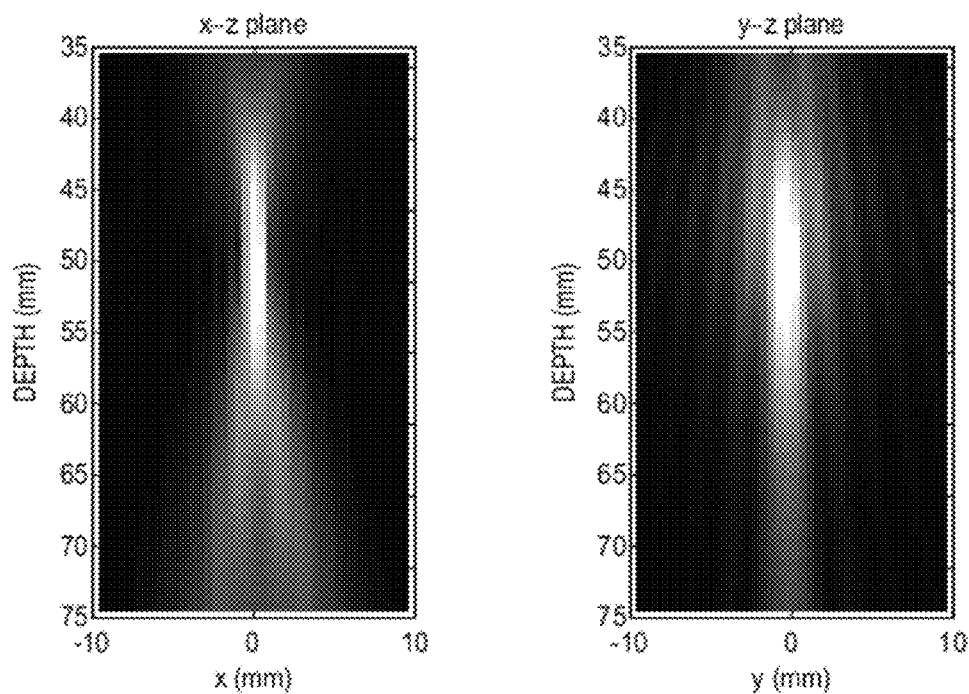
FIG. 5 is a series of images depicting an exemplary intensity field produced by a focused ultrasound beam with a focal depth of fifty millimeters.

The force density, F, exerted by ultrasound energy on tissue for shear wave generation is determined by the intensity, I, of the ultrasound:

$$F = \frac{2\alpha I}{c}; \tag{4}$$

where $\alpha$ and c are the attenuation coefficient and propagation speed of ultrasound, respectively. These properties can generally be assumed to be constants for different tissue types. Therefore, the force density field, F, is linearly proportional to the intensity field, I, of the ultrasound push beam. FIG. 5 illustrates an example of an intensity field of a C4-2 transducer focusing at 50 mm from the transducer surface. The left image panel shows a two-dimensional slice of the intensity field in the axial-lateral plane. The right image panel shows a two-dimensional slice of the intensity field in the axial-elevational plane, which corresponds to an out-of-plane slice in the left image panel. It can be seen in FIG. 5 that the concentrated area of the force field is close to a line force; thus, the assumptions of the shear wave speed analysis mentioned above are relatively well met.

Figure 6:
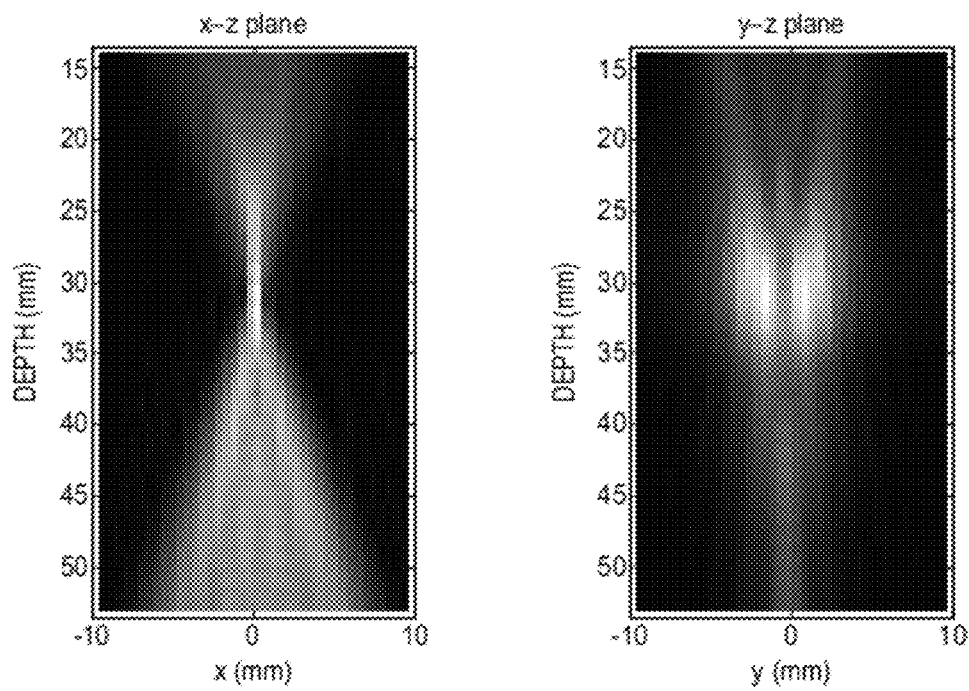
FIG. 6 is a series of images depicting an exemplary intensity field produced by a focused ultrasound beam with a focal depth of thirty millimeters.

FIG. 6 illustrates an example of an intensity field of the same C4-2 transducer when it is focused at 30 mm instead of the 50 mm in FIG. 5. It can be seen that the force distribution in this example is not a line force; rather, the max intensity splits into two separate peaks symmetric and away from the center plane of the transducer. The C4-2 transducer uses an acoustic lens to provide a fixed elevational focus at about 70 mm away from the transducer surface. This leads to poorly focusing in the elevation direction when the beam is focused too close to the transducer, as shown in FIG. 6.

Figure 7:
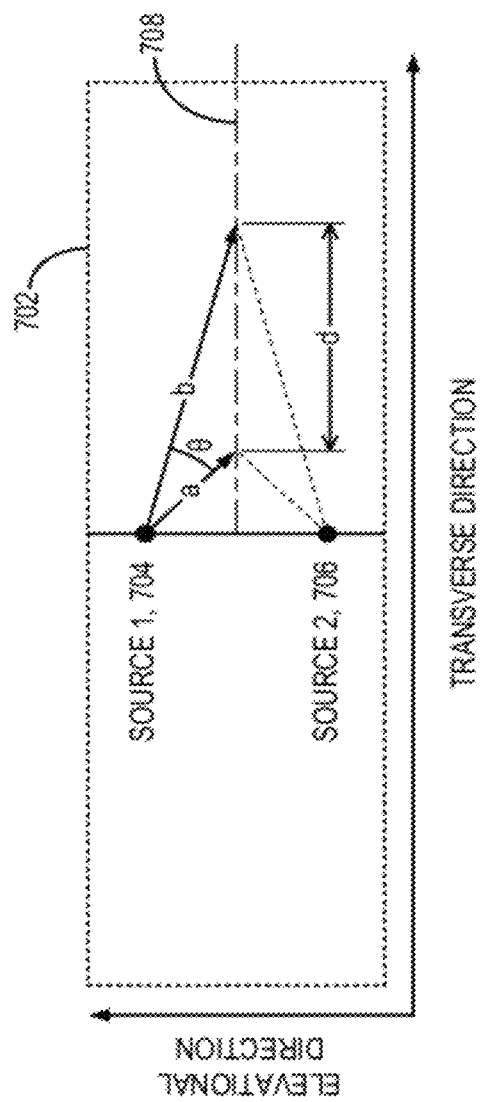
FIG. 7 is a pictorial representation of bias being introduced into shear wave speed measurements resulting from split intensity field peaks in the elevation direction.

The force field of FIG. 6 can be simplified to two line forces, as illustrated in FIG. 7 to illustrate the bias on shear wave speed measurements. FIG. 7 shows the two line forces in a focal plane perpendicular to the axis of the transducer; that is, in an out-of-plane slice at the focus depth, $d_f$, such as the one shown in FIG. 1. The rectangular broken line box 702 represents transducer with its ultrasound beam directed into the image plane. The line forces are also directed into the image plane and, therefore, are represented by two dots: source one 704 and source two 706. Shear wave speed is estimated from the arrival time along the mid-elevational line 708. For clarity purposes, the shear waves emanating from source two 706 are only shown as dashed lines in FIG. 7. The shear wave travels distances a and b in times $t_1$ and $t_2$, respectively, to intersect with the mid-elevational line 708 where detection is made. If the real shear wave speed of the medium is $c_0$, then:

$$a = c_0 t_1 \quad (5);$$

and $$b = c_0 t_2 \quad (6).$$

However, the apparent shear wave speed determined by measuring the arrival time along the mid-elevational line 708 is:

$$\begin{aligned}\tilde{c} &= \frac{d}{t_2 - t_1} \\ &= \frac{\sqrt{a^2 + b^2 - 2ab\cos\theta}}{t_2 - t_1} \geq \frac{\sqrt{a^2 + b^2 - 2ab}}{t_2 - t_1} \\ &= \frac{b - a}{t_2 - t_1} \\ &= \frac{c_0 t_2 - c_0 t_1}{t_2 - t_1} \\ &= c_0; \end{aligned} \quad (7)$$

Therefore, the measured shear wave speed, $\tilde{c}$, is biased such that it is greater than the true shear wave speed, $c_0$. This bias is position dependent. For example, the bias is larger closer to the sources and smaller when far away from the sources.

In addition to the three-dimensional shape of the ultrasound push beam, the ultrasound detection beam used for shear wave detection also has a three-dimensional distribution. This means that pulse-echo detection cannot measure tissue motion at an infinitesimal point, but rather measures the averaged tissue motion within the small, but finite, detection beam dimension. This three-dimensional structure of the ultrasound detection beam can also have an impact on shear wave speed estimation. The overall result is that shear wave speed measurements are influenced by the beam shape of the ultrasound used for shear wave generation, as well as that used for detection. The ultrasound beam shape depends on where the ultrasound energy is electronically focused; therefore, shear wave speed measurements will be position dependent, even in a media with uniform stiffness, and, thus, a uniform shear wave speed.

Generally, shear wave speed measurements are depth dependent and biased towards overestimation. For example, at a measurement depth of 70 mm with a C4-2 transducer, the measured shear wave speed is close to the true value because there will be no split peaks of the force field at this focal depth.

Shear wave speed measurements can also depend on the distance between the push beam and the detection location. In general, measured shear wave speed is higher when detection is closer to the push beam and, thus, overestimated. This overestimation is exacerbated at shallow focal depths where the force field has split peaks.

Figure 8:
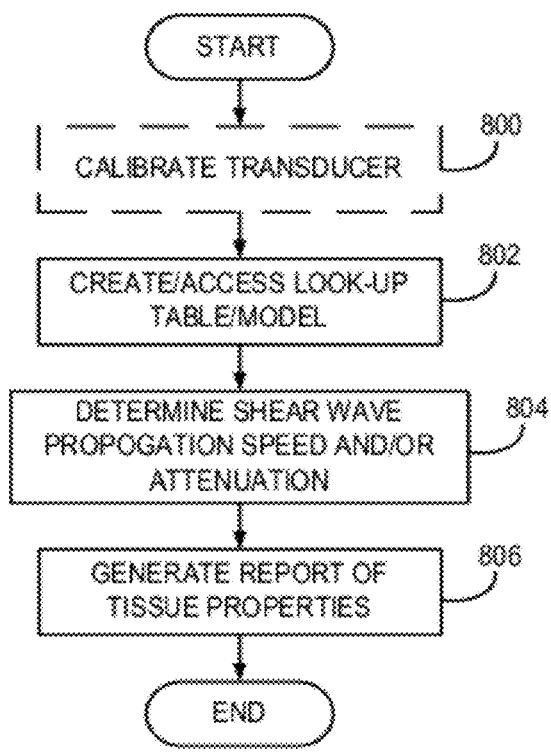
FIG. 8 is a flow chart setting forth the steps of an exemplary method in accordance with the present invention.

Referring to FIG. 8, a method is provided herein for correcting these systematic biases in shear wave speed measurements. The process begins at process block 800 by optionally calibrating a transducer. In one embodiment, multiple test blocks with known shear wave speeds are used to calibrate shear wave speed measurements for a given ultrasound transducer. These test blocks are preferably homogenous with similar ultrasound properties, such as attenuation, speed, and scattering characteristics as compared to tissues. Each block preferably has a different shear wave speed. In addition, the shear wave speed of any given block may be frequency independent, such as for a purely elastic medium, or frequency dependent, such as for a viscous medium. Shear wave speeds of all test blocks will, therefore, preferably evenly cover the range of shear wave speeds expected in a particular application. The transducer under test is used to make measurements within each block at different depths and steered angles of the ultrasound beam. The results of these tests are then used to generate a look-up table indicating the amount of bias at each measurement location in materials of different stiffness. Thus, at process bock 802, depending upon whether process bock 802 was currently performed or previously performed for a given transducer, the look-up table is created and/or accessed. Interpolation schemes can be used to predict biases at slightly different material stiffness and measurement positions not covered in the tests or stored in an accessed look-up table. Such a look-up table can be used in real measurements to retrospectively correct for shear wave speed. Such corrections cover the bias caused by the push beam and the detection beam.

Of course, other substitutes for the look-up table are contemplated and may be saved in a variety of formats, including a matrix, list, model, and the like. For example, another embodiment of the correction method does not use a look-up table for correction, but rather utilizes mathematical modeling for the correction. The intensity field of an ultrasound transducer can be calculated from software programs, such as the FIELD II program described by J. A. Jensen in "Field: A Program for Simulating Ultrasound Systems," *Medical & Biological Engineering & Computing*, 1996; 34:351-353, supplement 1, part 1, and by J. A. Jensen and N. B. Svendsen in "Calculation of Pressure Fields from Arbitrarily Shaped, Apodized, and Excited Ultrasound Transducers," *IEEE Trans. Ultrason., Ferroelec., Freq. Contr.*, 1992; 39:262-267. This model intensity field is used to calculate the force field from the transducer using, for example, Eqn. (4) above. Shear waves generated by the force field can be calculated by known finite element methods ("FEMs"), as is described, for example, by M. L. Palmeri, et al., in "A Finite-Element Method Model of Soft Tissue Response to Impulsive Acoustic Radiation Force," *IEEE Trans. Ultrason. Ferroelectr. Freq. Control,* 2005; 52:1699-1712, or by using Green's function, as is described, for example, by J. Bercoff, et al., in "The Role of Viscosity in the Impulse Diffraction Field of Elastic Waves Induced by the Acoustic Radiation Force," *IEEE Trans. Ultrason. Ferroelectr. Freq. Control,* 2004b; 51:1523-1536. Bias due to measuring the shear wave speed at the mid-elevational plane of the transducer is, thus, calculated and used to correct measurements in real tissues at any depth, any steered angle, and any tissue stiffness range. To further improve the correction accuracy, tissue motion averaging due to the three-dimensional beam shape of the detection ultrasound beam may also be considered, using, for example, a method such as the one described by M. L. Palmeri, et al., in "Ultrasonic Tracking of Acoustic Radiation Force-Induced Displacements in Homogeneous Media," *IEEE Trans. Ultrason. Ferroelectr. Freq. Control,* 2006; 53:1300-1313. This can be achieved by simulation through software programs such as the FIELD II program mentioned above.

Referring again to FIG. 8, regardless of when or in what particular format the correction for the ultrasound beam shape is created or stored, the process continues, generally, with a method for estimating tissue stiffness and viscosity. Specifically, the method uses the correction data created/accessed at process block 802 to determine shear wave propagation speed and/or attenuation at process block 804 and, using these determinations, to generate a report on tissue properties at process block 806, such as tissue stiffness and/or viscosity.

According to the Voigt model, shear wave propagation speed, $c_s$, is given by:

$$c_s(\omega_s) = \sqrt{\frac{2(\mu_1^2 + \omega_s^2\mu_2^2)}{\rho\left(\mu_1 + \sqrt{\mu_1^2 + \omega_s^2\mu_2^2}\right)}} \quad (8)$$

where $\omega_s$ is the angular frequency of the shear wave and $\rho$, $\mu_1$, and $\mu_2$ are the density, shear modulus, and viscosity of the medium, respectively. Eqn. (3) is a special case of Eqn. (8), in which tissue viscosity is assumed to be zero. Also according to the Voigt model, the shear wave attenuation, $\alpha_s$, can be given by:

$$\alpha_s(\omega_s) = \sqrt{\frac{\rho\omega_s^2\left(\sqrt{\mu_1^2 + \omega_s^2\mu_2^2} - \mu_1\right)}{2(\mu_1^2 + \omega_s^2\mu_2^2)}}. \quad (9)$$

Tissue shear wave speed, $c_s$, can be measured at multiple frequencies; that is, measuring the dispersion or frequency dependence of the shear wave speed, and fit with Eqn. (8) to calculate shear modulus and viscosity of tissue. Additionally, shear wave attenuation and speed can also be used together to calculate $\mu_1$ and $\mu_2$. Rearranging Eqns. (8) and (9), the following equations are determined, which can be used to calculate $\mu_1$ and $\mu_2$ at a single frequency:

$$\mu_1 = \frac{\rho c_s^2 \omega_s^2 (\omega_s^2 - \alpha_s^2 c_s^2)}{(\omega_s^2 + \alpha_s^2 c_s^2)^2}; \quad (10)$$

and $$\mu_2 = \frac{2\rho c_s^2 \omega_s^2 \alpha_s}{(\omega_s^2 + \alpha_s^2 c_s^2)}. \quad (11)$$

Utilizing the Voigt model of Eqn. (8) requires measuring shear wave speed over a range of frequencies. Shear waves generated by an ultrasound push beam have many frequency components; therefore, using this approach usually requires measuring shear wave speed at weak frequency components where the measurements are not reliable and, therefore, will often introduce errors in the measurements. By using Eqns. (10) and (11), the strongest frequency component of the shear wave can be selected for the calculation of stiffness and viscosity so that the results are less susceptible to noise.

Figure 9:
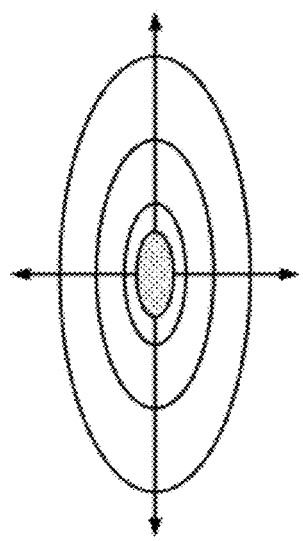
FIG. 9 is a pictorial representation of shear waves produced by an ultrasound push beam at the focal plane of the ultrasound beam.

To measure shear wave attenuation, errors arising from the geometric effect are preferably corrected for. FIG. 9 shows an exemplary profile of an ultrasound push beam at its focal plane. The ultrasound propagation direction is out-of-plane in FIG. 9. Shear waves are generated by the push beam and propagate outwards from the focal region in all directions. As the shear wave propagates outwards, its amplitude decreases because its energy is being spread over larger areas, which are denoted by larger ovals in FIG. 9. This effect can be considered as geometric attenuation. On the other hand, the attenuation values to be measured for Eqns. (10) and (11) are due to tissue viscosity. As the shear wave propagates outwards, its decrease in amplitude is due to both geometric and viscous attenuation. The geometric attenuation needs to be accounted for in order to more reliably measure the viscous attenuation correctly.

To estimate the geometric attenuation, an assumption is made that the geometric attenuation introduces a weighting factor of $1/\sqrt{r}$ on the shear wave amplitude, where r is the propagation distance of the shear wave from the push origin. A more accurate approach is to calculate the intensity field of the ultrasound beam, such as by using software such as the FIELD II software described above. This modeled intensity field can then be used to simulate the propagation of the shear wave in a pure elastic medium using FEMs or Green's function. By setting the viscosity of the medium to zero in such simulations, the decrease of the shear wave amplitude is only due to geometric effects. Such simulations require the knowledge of medium stiffness, which can be estimated from the shear wave speed using Eqn. (3).

The present invention has been described in terms of one or more preferred embodiments, and it should be appreciated that many equivalents, alternatives, variations, and modifications, aside from those expressly stated, are possible and within the scope of the invention.

The invention claimed is:

1. A method for measuring mechanical properties of a tissue, the steps of the method comprising:
    a) applying with an ultrasound system, ultrasound energy to the tissue in order to produce shear waves that propagate therein;
    b) acquiring measurement data from the shear waves by directing ultrasound detection pulses into the tissue with the ultrasound system;

c) obtaining information about the intensity field produced by the ultrasound energy applied in at least one of step a) and step b);

d) producing a correction factor using the information about the intensity field obtained in step c);

e) correcting the measurement data acquired in step b) for errors arising from a geometry of the ultrasound energy applied in at least one of step a) and step b) by applying the correction factor produced in step d) to the measurement data acquired in step b); and f) generate a report of mechanical properties of the tissue using the corrected measurement data produced in step e).

2. The method as recited in claim 1 in which step c) includes obtaining the information by mathematically modeling the intensity field and effects of the intensity field on shear wave speed measurements.

3. The method as recited in claim 1 in which step c) includes obtaining intensity field information related to the ultrasound detection pulses applied in step b); step d) includes producing another correction factor using the intensity field information related to the ultrasound detection pulses; and step e) further includes correcting the measurement data acquired in step b) for errors arising from a geometry of the ultrasound detection pulses applied in step b) using the another correction factor produced in step d).

4. A method for measuring mechanical properties of a tissue, the steps of the method comprising:
a) applying with an ultrasound system, ultrasound energy to the tissue in order to produce shear waves that propagate therein;
b) acquiring measurement data from the shear waves by directing ultrasound detection pulses into the tissue with the ultrasound system;
c) obtaining a correction factor by interrogating a look-up table containing shear wave speed measurements acquired from multiple locations within each of a plurality of different tissue phantoms having known mechanical properties;
d) correcting the measurement data acquired in step b) for errors arising from a geometry of the ultrasound energy applied in at least one of step a) and step b) by applying the correction factor obtained in step c) to the measurement data acquired in step b); and
e) generate a report of the mechanical properties of the tissue using the corrected measurement data produced in step d).

5. The method as recited in claim 4 in which the known mechanical properties of the plurality of different tissue phantoms include at least one of stiffness and viscosity.

6. A method for measuring mechanical properties of a tissue, the steps of the method comprising:
a) applying with an ultrasound system, ultrasound energy to the tissue in order to produce shear waves that propagate therein;
b) acquiring measurement data from the shear waves by directing ultrasound detection pulses into the tissue with the ultrasound system; and
c) calculating mechanical properties of the tissue using a model that relates the acquired measurements data and only one shear wave frequency to the mechanical properties.

7. The method as recited in claim 6 in which the mechanical properties include at least one of stiffness and viscosity.

8. The method as recited in claim 6 in which the single shear wave frequency used by the model in step c) is selected as a strongest frequency component of the shear waves produced in step a) so that the calculated mechanical properties are less susceptible to noise.

9. A system for measuring mechanical properties of a tissue comprising:
an ultrasound system configured to deliver ultrasound energy to the tissue in order to produce shear waves that propagate therein and direct ultrasound detection pulses into the tissue to acquire measurement data from the shear waves;
a memory having stored therein shear wave speed measurements acquired from multiple locations within each of a plurality of different tissue phantoms having known mechanical properties; and
a processor configured to receive the measurement data from the ultrasound system and access the memory to receive the shear wave speed measurements, the processor programmed to:
determine a correction factor using the shear wave speed measurements;
correct the measurement data for errors arising from a geometry of the ultrasound energy applied using the correction factor; and
calculate mechanical properties of the tissue using the corrected measurement data.

10. The system as recited in claim 9 in which the known mechanical properties of the plurality of different tissue phantoms include at least one of stiffness and viscosity.

11. A system for measuring mechanical properties of a tissue comprising:
an ultrasound system configured to deliver ultrasound energy to the tissue in order to produce shear waves that propagate therein and direct ultrasound detection pulses into the tissue to acquire measurement data from the shear waves; and
a processor configured to:
obtain information about the intensity field produced by the delivery of ultrasound energy to the tissue in order to produce the shear waves;
determine a correction factor using the information about the intensity field;
generate corrected measurement data having reduced errors arising from a geometry of the ultrasound energy delivered to the tissue in order to produce the shear waves using correction factor; and
determine mechanical properties of the tissue using the corrected measurement data.

12. The system as recited in claim 11 in which the processor is further configured to mathematically model the intensity field and effects of the intensity field on shear wave speed measurements.

13. The system of claim 11 further comprising a memory having stored therein shear wave speed measurements acquired from multiple locations within each of a plurality of different tissue phantoms having known mechanical properties and wherein the processor is further configured to access the memory to determine the correction factor.

* * * * *